(12) United States Patent
MacKeen

(10) Patent No.: US 6,254,893 B1
(45) Date of Patent: *Jul. 3, 2001

(54) COMPOSITION FOR TREATING DRY EYE

(75) Inventor: Donald L. MacKeen, Bethesda, MD (US)

(73) Assignee: DEO Corporation, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/177,903

(22) Filed: Oct. 23, 1998

Related U.S. Application Data

(60) Division of application No. 08/785,080, filed on Jan. 21, 1997, now Pat. No. 5,830,508, which is a continuation-in-part of application No. 08/144,643, filed on Oct. 28, 1993, now Pat. No. 5,595,764, which is a continuation of application No. 07/986,932, filed on Dec. 8, 1992, now Pat. No. 5,366,739, which is a continuation-in-part of application No. 07/926,244, filed on Aug. 6, 1992, now Pat. No. 5,290,572.

(51) Int. Cl.$^7$ .......................... A61K 33/06; A61K 33/10; A61K 31/194; A61K 9/14; A61K 47/00
(52) U.S. Cl. ..................... 424/602; 424/400; 424/484; 424/489; 424/500; 424/501; 424/502; 424/602; 424/603; 424/682; 424/686; 424/687; 424/696; 514/574; 514/912; 514/914; 514/915; 514/951
(58) Field of Search ................................ 424/601–603, 424/678, 682, 686–689, 693, 696, 484, 489, 500, 501, 502, 400; 514/63, 557, 574, 578, 912, 914, 915, 951

(56) References Cited

U.S. PATENT DOCUMENTS

| | | | |
|---|---|---|---|
| 3,991,759 | * | 11/1976 | Urquhart . |
| 4,579,131 | * | 4/1986 | Syed . |
| 4,775,531 | * | 10/1988 | Gilbard . |
| 4,781,915 | * | 11/1988 | Maruya et al. . |
| 4,966,773 | * | 10/1990 | Gressel et al. . |
| 5,290,572 | * | 3/1994 | Mackeen .............................. 424/602 |
| 5,366,739 | * | 11/1994 | Mackeen .............................. 424/602 |
| 5,595,764 | * | 1/1997 | Mackeen .............................. 424/687 |

FOREIGN PATENT DOCUMENTS

| | | |
|---|---|---|
| 258865A2 | 3/1988 | (EP) . |
| 0473159A1 | 3/1992 | (EP) . |
| 1070593A | 7/1967 | (GB) . |
| WO 8901772A | 3/1989 | (WO) . |

OTHER PUBLICATIONS

Database Dialog, File 636 Online! Abstract 1261920, XP002017790, "Bausch & Lomb Dry Eye Therapy Lubricating Eye Drops Manufacture," Product Alert, vol. 21, Oct. 28, 1991.

Database WPI, Abstract, Derwent Publications Ltd., Section Ch., Week 199113, London, GB; Class B05, An 1991–092243, XP002138757 and JP 03 038519 A, Taisho Pharm. Co. Ltd., Feb. 19, 1991.

Hardberger, R., M.D. et al., "Effects of Drug Vehicles on Ocular Contact Time," *Arch. Ophthalmol.,* 93(1):42–45, Jan. 1975.

Seig, James W. et al., "Vehicle Effects on Ocular Drug Bioavailability II: Evaluation of Pilocarpine," *Journal of Pharmaceutical Sciences,* 66(9):1222–1228, Sep. 1977.

Sugaya, Makoto et al., "Kinetics of Topical Pilocarpine in the Human Eye," *Jpn. J. Ophthalmol.,* 22(1):127–141, 1978, XP000607513.

Promt Abstract, Accession No. 9/: 35285, 1990.*

MacKeen, Donald L., "Aqueous Formulations and Ointments," IN: Holly, Frank J. (Ed.), Clinical Pharmacology of the Anterior Segment, Little, Brown and Company, Boston, vol. 20, No. 3, pp. 79–81,1980.*

Physicians' Desk Reference for Ophthalmology, 16$^{th}$ ed., pp. 9,11,12,13, 153, 154, 1988.*

Remington's Pharmaceutical Sciences, 18$^{th}$ ed., Mack Publishing Co., PA, pp. 1581–1595, 1990.*

* cited by examiner

*Primary Examiner*—John Pak
(74) *Attorney, Agent, or Firm*—David A. Farah; Sheldon & Mak

(57) ABSTRACT

A calcium-based ophthalmic composition for treating dry eye including a hydrophobic carrier, such as petrolatum, and a calcium salt. Also a method for treating dry eye comprising the step of administering the composition according to the present invention.

2 Claims, 6 Drawing Sheets

FIG. 1

| AGE GROUP | 20-39 | | 40-59 | | 60-79 | | 80-88 | |
|---|---|---|---|---|---|---|---|---|
| SIGNS | M | F | M | F | M | F | M | F |
| CONJUNCTIVAL INJECTION/ CHEMOSIS | 2 | 4 | 8 | 12 | 10 | 11 | 2 | 2 |
| DEBRIS ON LASHES | 2 | 2 | 7 | 10 | 10 | 10 | 2 | 2 |
| TBUT < 5 SEC* | 1 | 2 | 6 | 8 | 6 | 8 | 2 | 1 |
| SWOLLEN LIDS | 1 | 2 | 2 | 2 | 4 | 7 | 2 | 2 |
| ROSE BENGAL STAINING | 0 | 1 | 3 | 4 | 8 | 9 | 1 | 2 |
| FLUORESCEIN STAINING OF CORNEA | 1 | 2 | 1 | 4 | 7 | 9 | 2 | 1 |
| CLOUDY OR PASTY MEIBOMIAN LIPIDS SEEN ON LID COMPRESSION | 1 | 2 | 2 | 2 | 4 | 7 | 2 | 2 |
| STRANDS ON CORNEAL SURFACE | 0 | 1 | 2 | 2 | 3 | 6 | 1 | 2 |
| SYMPTOMS | | | | | | | | |
| ITCHING | 2 | 1 | 1 | 8 | 7 | 9 | 2 | 2 |
| BURNING | 1 | 3 | 1 | 4 | 1 | 3 | 1 | 2 |
| GRITTINESS | 0 | 1 | 3 | 3 | 0 | 4 | 1 | 0 |
| TOTAL NO. PATIENTS PER GROUP | 2 | 4 | 8 | 11 | 10 | 21 | 2 | 2 |

* ENTRANCE CRITERION, TBOT < 9 SEC. EACH PATIENT MAY HAVE HAD MORE THAN ONE SIGN/SYMPTOM; THEREFORE, THESE TOTALS MAY BE GREATER THAN THE NUMBER OF PATIENTS

FIG. 5

| WEEKS OF TREATMENT | | | | | | | | | | |
|---|---|---|---|---|---|---|---|---|---|---|
| | 1 | 2 | 3 | 4 | 5 | 6 | 7 | 8 | 9 | 10 |
| RESPONSES * | | | | | | | | | | |
| IMPROVEMENT IN SIGNS AND SYMPTOMS | 40 | 10 | 2 | 2 | 2 | 2 | 1 | - | - | - |
| MINIMAL IMPROVEMENT IN SIGNS AND SYMPTOMS | 58 | - | - | - | - | - | - | - | - | - |
| IMPROVEMENT IN SIGNS | 40 | 10 | 8 | 1 | - | - | - | - | - | - |
| NO IMPROVEMENT IN SIGNS AND SYMPTOMS | - | - | - | - | - | - | - | - | - | 2 |
| WORSENED STATUS | 1 | - | - | - | - | - | - | - | - | - |

* PATIENTS MAY HAVE EXHIBITED ONE OR MORE CHANGES; THUS THE TOTAL MAY NOT EQUAL 60.

FIG. 6

| AGE | TOTAL SUCCESS | | PARTIAL SUCCESS | | FAILURE | |
|---|---|---|---|---|---|---|
| | MALE | FEMALE | MALE | FEMALE | MALE | FEMALE |
| 20-39 | 2 | 4 | 0 | 0 | 0 | 0 |
| 40-59 | 4 | 6 | 3 | 5 | 1 | 0 |
| 60-79 | 8 | 12 | 2 | 8 | 0 | 1 |
| > 80 | 2 | 2 | 0 | 0 | 0 | 0 |

COMPOSITION FOR TREATING DRY EYE

CROSS-REFERENCE TO RELATED APPLICATIONS

The present Application is a Divisional of U.S. patent application Ser. No. 08/785,080 entitled COMPOSITION FOR TREATING DRY EYE, filed Jan. 21, 1997, now U.S. Pat. No. 5,830,508, which is a Continuation-in-Part of U.S. patent application Ser. No. 08/144,643 entitled OPHTHALMIC COMPOSITION FOR TREATING DRY EYE, filed Oct. 28, 1993, now U.S. Pat. No. 5,595,764, which is a continuation of U.S. patent application Ser. No. 07/986,932, entitled OPHTHALMIC COMPOSITION FOR TREATING DRY EYE, filed Dec. 8, 1992, now U.S. Pat. No. 5,366,739, which is a continuation in part of U.S. patent application Ser. No. 07/926,244, entitled OPHTHALMIC COMPOSITION FOR TREATING DRY EYE, filed Aug. 6, 1992, now U.S. Pat. No. 5,290,572, the contents of which are incorporated herein by reference in their entirety.

BACKGROUND

Dry eye, also known as keratoconjunctivitis sicca, is a common ophthalmological disorder affecting millions of Americans. The condition is particularly widespread among post-menopausal women due to hormonal changes following the cessation of fertility. It is one of the most common of human eye diseases and is generally treated through the topical delivery of a variety of therapeutic agents.

Dry eye may afflict an individual in varying severity. In mild cases, a patient may experience burning, a feeling of dryness, and persistent irritation when debris lodge between the eye lid and the eye surface. In severe cases, vision can be substantially impaired.

Although it appears that dry eye can result from a number of unrelated pathogenic causes, all presentations of the syndrome have in common the breakdown of the pre-ocular tear film. This breakdown results in dehydration of the exposed cornea and conjunctiva and many of symptoms associated with dry eye.

Eye care practitioners have taken several approaches to the treatment of dry eye. One common approach has been to supplement and stabilize the preocular tear film using artificial tears. Another approach has been the use of ocular inserts that function to provide a tear substitute or to stimulate endogenous tears.

Examples of the tear substitution approach include the use of buffered, isotonic saline solutions, and aqueous solutions containing water soluble polymers that render the solutions more viscous and thus less easily shed by the eye. Tear reconstitution is also attempted by providing one or more components of the tear film such as phospholipids. Another recent approach involves the provision of lubricating substances in lieu of artificial tears. Other treatments involve the use of hormones, such a conjugated estrogens, to treat dry eye in post-menopausal women.

Although these approaches have met with some success, there remains problems in the treatment of dry eye. The use of tear substitutes, for example, generally requires many repeated applications over the course of a patient's waking hours. It is not uncommon for a patient to have to apply artificial tear solution ten to twenty times over the course of the day. Such dosing is cumbersome and time consuming, increases the exposure of the eye to preservative agents present in many artificial tears.

Similarly, ocular inserts are often difficult to insert and uncomfortable when used as intended. Further, as foreign bodies, ocular inserts pose a risk of acting as a vector for infectious organisms.

Therefore, there remains a need for a safe and effective treatment for dry eye. Ideally, the treatment should be capable of treating dry eye due to a variety of causes. Further, the treatment should not require the application of a drug on a very frequent basis, and should be easy to use. Also, the treatment should not cause discomfort itself and should cause minimal blurring, if any.

SUMMARY

According to one embodiment of the present invention, there is provided a calcium-based ophthalmic composition for treatment of dry eye syndrome. The calcium-based ophthalmic composition includes an ophthalmologically acceptable hydrophobic carrier and an ophthalmologically acceptable calcium salt dispersed in the carrier. The hydrophobic carrier is preferably petrolatum or a combination of petrolatum and white wax. The calcium salt is preferably selected from the group consisting of calcium carbonate, calcium sulfate, calcium tartrate, calcium magnesium carbonate, calcium metasilicate, calcium malate, secondary calcium orthophosphate, or a combination of the preceding.

According to another embodiment of the present invention, there is provided a method of treating a patient with dry eye comprising the step of administering a calcium-based ophthalmic composition according to present invention to the patient's eye, eye lid or to the skin surrounding the patient's eye. In a preferred embodiment, the composition is administered to the lateral portion of the lower eyelid.

BRIEF DESCRIPTION OF THE DRAWINGS

These and other features, aspects and advantages of the present invention will become better understood with regard to the following description, appended claims, and accompanying figures where:

FIG. 1 is a table listing the signs and symptoms observed at the initial examination of patients who underwent a clinical trial of the calcium-based pharmaceutical composition according to one embodiment of the present invention;

FIG. 5 is a table listing the improvements in signs and symptoms observed during daily treatment with the calcium-based pharmaceutical composition during the clinical trial; and FIG. 6 is a table listing the outcome of the patients whose therapies were monitored during the clinical trial.

DESCRIPTION

Figure 2:
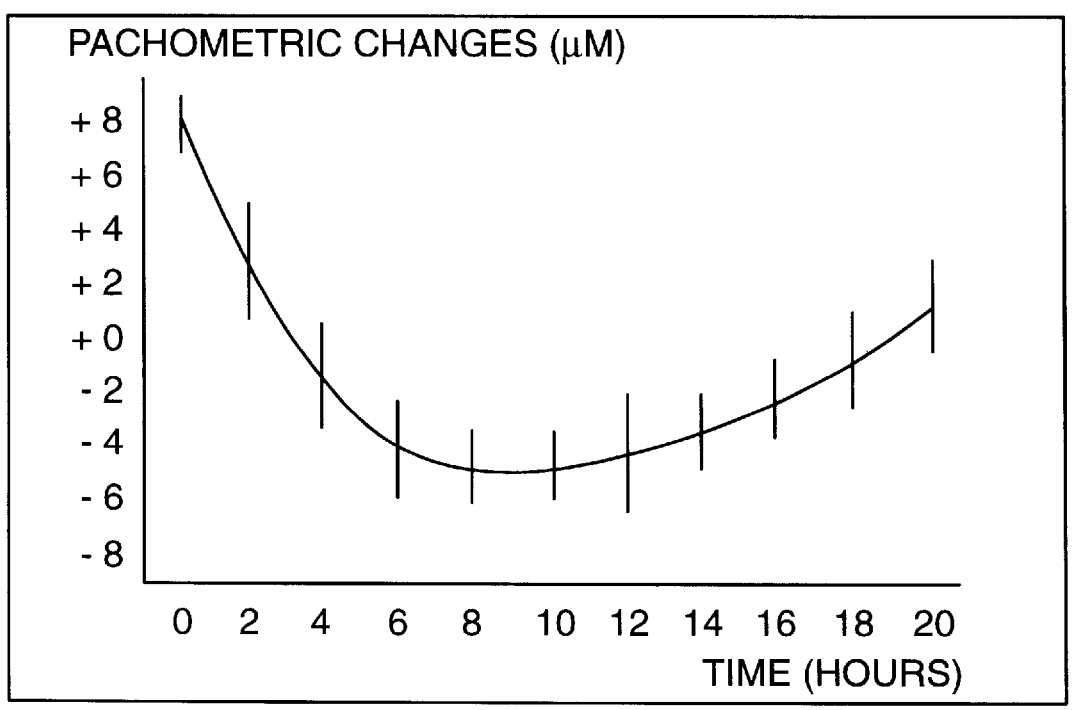
FIGS. 2 to 4 are graphs demonstrating the changes in corneal thickness, TBUT, and height of the lower meniscus, respectively, in 15 of the 60 patients following the first application of the calcium-based pharmaceutical composition during the clinical trial.

According to one aspect of the present invention, there is provided a method of delivering a pharmaceutical composition to the eye. The method includes the step of placing the pharmaceutical composition on the skin adjacent to the lateral canthus or on the lateral portion of the lower eyelid margin. Placement of the pharmaceutical agent is accomplished manually or by a suitable applicator, such as a cotton swab. Movements of the extra-ocular muscles involved in the blink response transport a portion of the composition into the interpalpebral space. The drug is then released by dissolution into the tear film to treat diseases and conditions of the cornea and adnexa. Drugs with the chemical capacity to pass through corneal tissue can also enter the eye to treat diseases and conditions within the eye.

Dosages of pharmaceutical compositions delivered by this method do not depend directly on the amount of the composition placed on the skin adjacent to the lateral canthus or on the lateral portion of the lower eyelid margin because only a small portion of the composition is delivered during each blink. Dosing of the pharmaceutical composition can, therefore, be regulated by varying the time between applications.

The type of drug to be delivered according to the method disclosed herein as part of the pharmaceutical composition will depend primarily on the disease or condition to be treated. Examples of drugs that can be used with the method include drugs used to treat dry eye such as cyclosporine A, vitamin A alcohol, and testosterone; drugs used to treat glaucoma such as pilocarpine, beta blockers, and carbonic anhydrase inhibitors; and drugs used to treat keratopathies such as antifungals and antivirals. Other suitable drugs can be used as will be understood by those with skill in the art with reference to the disclosure herein.

Pharmaceutical compositions to be delivered by this method are prepared by mixing a suitable drug with a pharmacologically acceptable carrier. The appropriateness of the carrier is determined by its pharmacological acceptability for introduction onto or within the eye, and by the chemical characteristics of the drug that is to be admixed with the carrier.

Although the carrier can be a wide variety of compounds such as water-based solutions and gels, the preferred carrier is hydrophobic and will not readily evaporate in air. Carriers such as ophthalmological grade petrolatum and other water-free compounds are preferred because their use decreases or eliminates the need for preservatives. Petrolatum is particularly preferred as a carrier because it is hydrophobic, can be obtained in a suitable pure state, will not evaporate, and is an excellent solvent for lipids. Further, it is inert and non-interactive with ocular tissues.

Appropriate amounts of drug and carrier for preparation of the pharmaceutical composition can be determined by those with skill in the art with reference to the disclosure herein. Delivery of the drug can be extended over time by utilizing a chemical form of the drug that is at least partly insoluble in water. The greater the insolubility, the longer the drug will take to dissolve and, thus, come into contact with eye tissue.

According to another aspect of the present invention, there is provided an ophthalmic pharmaceutical composition for topical administration. The composition comprises a minimally water-soluble, calcium-based composition. The composition can be administered by application directly to the cornea or conjunctiva or can be administered in conjunction with ocular inserts or can be administered by placing the composition on the skin adjacent the eyelids, such as adjacent the lateral eyelid margins, or by placing the composition on the lateral portion of the lower eyelid margin.

The calcium salt is preferably largely insoluble in water to facilitate a slow release of calcium ion into the tear film. This decreases the need for continuous or frequent application of the composition. Suitable calcium salts include calcium carbonate ($CaCO_3$), calcium sulfate ($CaSO_4$), calcium tartrate ($CaC_4H_4O_6$), calcium magnesium carbonate ($CaCO_3 \cdot MgCO_3$), calcium metasilicate ($CaSiO_3$), calcium malate ($Ca_4H_4O_6$), secondary calcium orthophosphate ($CaHPO_4$), and similar poorly water soluble calcium salts that are physiologically compatible and stable. Among these calcium salts, calcium carbonate, with a solubility of 0.0014 gm/100 ml in cold water, is preferred.

In a preferred embodiment, the calcium salt is finely divided, preferably into microfine particles having a mean diameter of about 60 microns or less. In another preferred embodiment, the mean particle diameter is between about 10 to 60 microns.

The calcium-based pharmaceutical composition further includes a hydrophobic carrier. The hydrophobic carrier tends to supply calcium ion to the cornea and conjunctiva for a longer period than a typical hydrophilic carrier. Further, a composition having a hydrophobic carrier according to the present invention can be applied to the skin adjacent to the lateral canthus or on the lateral portion of the lower eyelid margin according to the methods disclosed herein.

The preferred carrier for a drug for treating dry eye is hydrophobic and sufficiently viscous to prevent dripping or running after application to the skin adjacent the eyelids. Further, using a hydrophobic, water-free carrier advantageously reduces or eliminates the need for a preservative. In a preferred embodiment, the carrier is petrolatum. The melting point of petrolatum can be increased by the admixture of a suitable substance such as white wax.

The pharmaceutical composition is prepared by mixing a poorly water-soluble calcium salt and a pharmacologically acceptable carrier. The calcium salt can be divided into microfine particles by any standard means, such as pulverization in a mortar and pestle. In a preferred embodiment, the composition is prepared by levigation with a polyol such as glycerol or propylene glycol. In a particularly preferred embodiment, levigation is performed with glycerol and light calcium carbonate in about a two to one ratio by weight. When prepared in this manner, a pharmaceutical composition according to the present invention can be prepared with final ratios by weight of light calcium carbonate/glycerol/petrolatum of approximately 1/2/7.

In another preferred embodiment, the composition includes an agent to enhance the interface between the hydrophilic polyol milieu surrounding the calcium salt and the hydrophobic carrier. Inclusion of the agent advantageously promotes stability and enhances transfer of the pharmaceutical composition while heated into containers. The agent can be selected from the group consisting of polyethylene glycol, glyceryl cocolate, sulfosuccinates, polysorbate 20, polysorbate 40, polysorbate 60, and polysorbate 80, or can be other suitable agents as will be understood by those with skill in the art with reference to the disclosure herein. In a preferred embodiment, the agent is anhydrous lanolin. In a particularly preferred embodiment, the agent is present in an amount less than about 0.5 percent by weight.

It will be apparent that the use of calcium ion to treat dry eye does not exclude the use of other known therapies. It is, therefore, within the scope of this invention to combine the delivery of calcium ion as disclosed herein with other drugs, such as retinoids, or estrogens. However, it is preferable to avoid combining the calcium-based composition of the present invention with drugs that include chelating or other binding agents having an affinity for ionic calcium as these combinations would decrease the efficacy of the calcium-based pharmaceutical composition disclosed herein.

When the pharmaceutical composition includes petrolatum as a carrier, sterilization is preferably accomplished by heating at about 120° C. for about 20 minutes in a suitable sterile container. Further, the composition is processed and stored in a manner which avoids exposing the petrolatum to ultraviolet radiation to avoid accelerating breakdown of the carrier.

A calcium-based pharmaceutical composition, according to the present invention, can be applied topically to the eye, either directly to the cornea or conjunctiva, indirectly by application to the skin adjacent to the eyelids or to the lateral portion of the lower eyelid margin, or through the use of an ocular insert or similar device. Although any of these methods of application are suitable, in a preferred embodiment the composition is applied to the lateral portion of the lower eyelid margin according to the method disclosed herein.

EXAMPLE

Clinical Trial Utilizing the Composition and Method According to the Present Invention A clinical trial was performed to determine the effects of a calcium-based pharmaceutical composition according to the present invention and the results were published in MacKeen, Donald L., Roth, Hans-Walter, A Preliminary Report on a New Method for the Treatment of Dry Eye, Practical Optometry 6:3, 1995, incorporated herein by reference in its entirety. In summary, the study group involved 60 patients with dry eye (22 males, 38 females), ranging in age from 20 to 88 years. The patients were unresponsive to conventional dry eye/blepharitis treatments. All 60 patients had chronic conjunctivitis and 58 had blepharitis. Referring now to FIG. 1, there is shown a table listing the signs and symptoms observed at the initial examination.

The pharmaceutical composition used to treat these patients contained calcium carbonate which was finely dispersed in a water-free vehicle consisting primarily of petrolatum according to the present invention. The composition was free of preservatives.

The pharmaceutical composition was administered by application to the skin of the lateral canthal area or streaked along the lateral portion of the lower eyelid margin. The patients were treated for between 1 and 12 weeks, with an average duration of treatment of between 14 and 21 days.

During the first 20 hours following initial administration of the pharmaceutical composition, each patient had central corneal thickness, tear break-up time and the height of the central lower meniscus measured. Follow-up tests included slit-lamp examination, expression of lower lid meibomian glands, assessment of subjective response, tear break-up time, Schirmer test I, rose bengal staining, and fluorescein staining.

The results of this study were as follows. Many patients reported an improvement in visual acuity shortly after application of the calcium-based pharmaceutical composition and symptomatic improvement in the first day of treatment. No patient reported blurring from the treatment.

Figure 3:
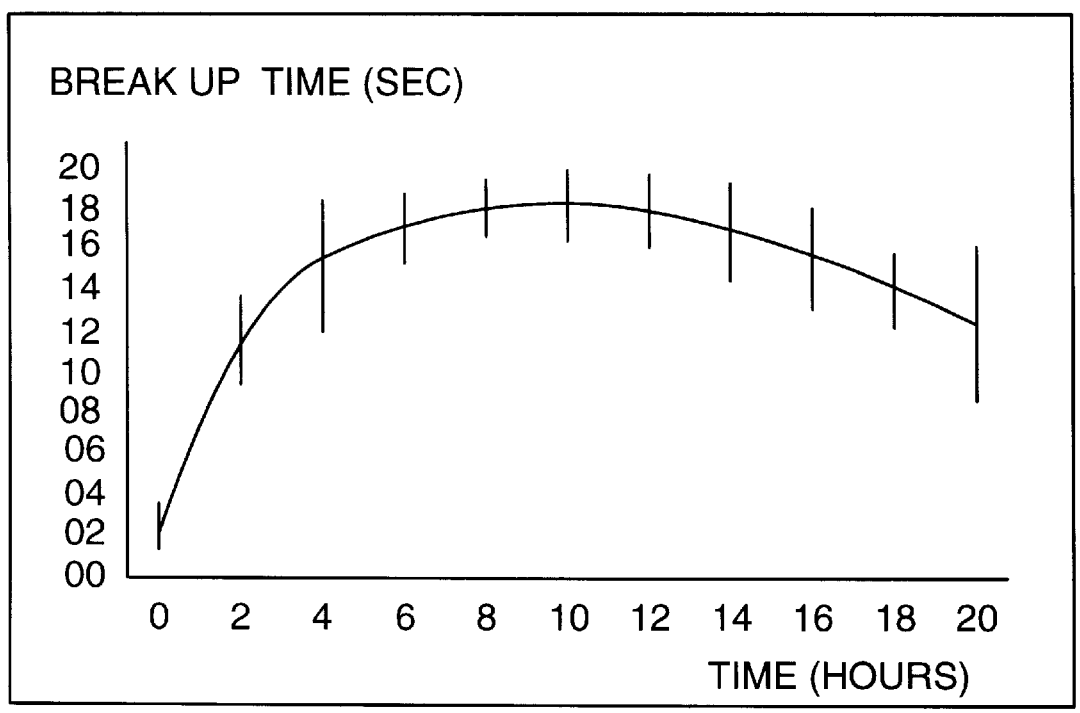
Figure 4:
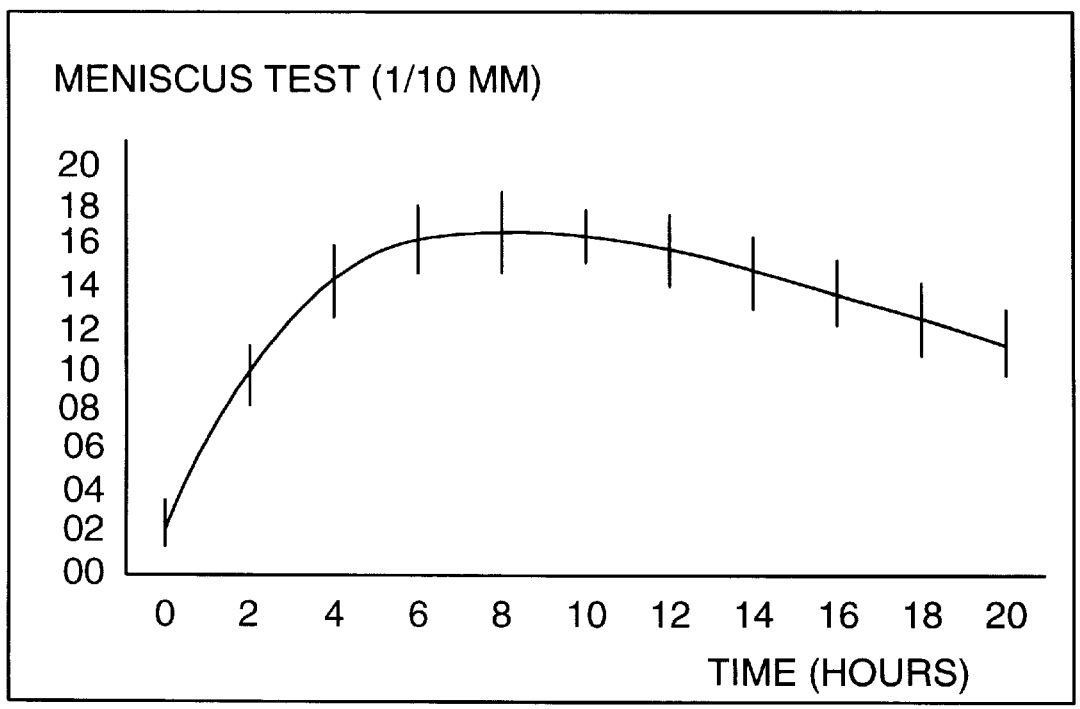

Referring now to FIGS. 2 to 4, the graphs shown demonstrate the changes in corneal thickness, TBUT, and height of the lower meniscus, respectively, in 15 of the 60 patients following the first application of calcium-based pharmaceutical composition. All of these measurements show statistically significant improvements.

As can be seen in FIG. 2, the average corneal thickness was $8\mu$ greater than the average normal (0 value on the ordinate) for this population of Europeans, 545 $\mu M \pm 20\mu$. Each error bar equals ±1 SD. The ordinate of the graph indicates corneal swelling or deswelling by positive and negative values respectively. Four hours following a single administration of the composition, the average corneal thickness value decreased below 0. The deswelling continued in time, and reached a maximum of approximately 5 $\mu M$ less than normal in an interval of 5 to 12 hours.

As can be seen in FIG. 3, the initial average tear break-up time (TBUT) was 2 seconds. The value increased rapidly to a maximum of 17 seconds in an 8 to 12 hour interval. By 20 hours, the value was still significantly greater than the starting value. The average value could be considered as normal by most criteria.

As can be seen in FIG. 4, meniscus height increased rapidly and reached a maximal value during an interval of 6 to 10 hours. At 20 hours the meniscus heights were still significantly greater than the starting value.

Many patients reported symptomatic improvement in one day. All experienced improvement within seven days of treatment.

Referring now to FIG. 5, there is shown a table listing the improvements in signs and symptoms observed during daily treatment. The improvement in signs included a decrease in conjunctival injection and chemosis, a decrease in lid swelling, a decrease in rose bengal staining, and an increase in TBUT. The improvement in symptoms included a decrease in burning, itching, and a feeling of grittiness.

Referring now to FIG. 6, there is shown a table listing the outcome of the patients whose therapeutic outcomes were a success, a partial success, or failure. As can be seen, ninety-seven percent of the patients obtained total or partial improvement. Sixty-seven percent of the patients experienced complete elimination of all signs and symptoms. Thirty percent of the patients experienced significant clinical improvement and obtained subjective relief.

Subjects with Schirmer values <1 mm per 5 minutes and corneal decompensation and those with severe allergies, e.g. atopy, did not respond to this therapy. However, these subjects reported that this treatment was neither worse nor better than previous treatments. One patient who failed this treatment was found to be sensitive to Vaseline® by skin testing.

During the early part of one study, supplies of the calcium-based pharmaceutical composition were not constant for each patient. As a result many patients went without the ointment, but retained temporary remissions without treatment which ranged from weeks to as long as six months.

Although the present invention has been discussed in considerable detail with reference to certain preferred embodiments, other embodiments are possible. Therefore, the spirit and scope of the appended claims should not be limited to the description of preferred embodiments contained herein.

I claim:

1. A calcium-based ophthalmic composition for treatment of dry eye syndrome consisting essentially of:

a) an ophthahmologically acceptable hydrophobic carrier selected from the group consisting of petrolatum and a combination of petrolatum and white wax; and b) dispersed within the carrier, one or more than one calcium salt selected from the group consisting of calcium carbonate, calcium sulfate, calcium tartrate, calcium magnesium carbonate, calcium metasilicate, calcium malate, secondary calcium orthophosphate;

where the composition is sufficiently viscous to prevent dripping or running after application to the skin adjacent the eyelids;

where the calcium salt has particles having a mean diameter of less than about 60 microns; and where the calcium salt is present in an amount of between about 2% and 25% by weight.

2. A method of treating a patient with dry eye comprising the step of administering an effective amount of the composition according to claim 1 to the patient's eye.

* * * * *